United States Patent [19]

Baldwin

[11] Patent Number: 4,581,335

[45] Date of Patent: Apr. 8, 1986

[54] PROCESS FOR PRODUCING A CLONED LUCIFERASE-SYNTHESIZING MICROORGANISM

[75] Inventor: Thomas O. Baldwin, Bryan, Tex.

[73] Assignee: Texas A&M University System, College Station, Tex.

[21] Appl. No.: 445,697

[22] Filed: Dec. 1, 1982

[51] Int. Cl.[4] ............ C12N 15/00; C12N 9/02; C12N 1/20; C12N 1/00
[52] U.S. Cl. .................. 435/172.3; 435/253; 435/317; 435/189; 935/27; 935/60
[58] Field of Search ............ 435/172.3, 253, 172, 435/317, 189; 935/27

[56] References Cited

PUBLICATIONS

Stuber et al., PNAS USA, vol. 78, pp. 167-171, Jan. 1981.
Belos et al., Science, vol. 218, pp. 791-793, Nov. 19, 1982.
Cohn et al., PNAS USA, vol. 80, pp. 120-124, Jan. 1983.
Lamfrom et al., Journal of Bacteriology, vol. 133, No. 1, pp. 354-363, (Jan. 1978).
Abstract of 82nd Annual Meeting of The American Society for Microbiology (ASMAC), #H123, Mar. 7-12, 1982.

Primary Examiner—Alvin E. Tanenholtz
Attorney, Agent, or Firm—Arnold, White & Durkee

[57] ABSTRACT

A process for producing a cloned luciferase-synthesizing microorganism, capable of the expression of bioluminescence, is disclosed. The process involves isolation and digestion of the genomic DNA of an appropriate bioluminescent microorganism, such as *Vibrio harveyi*, to obtain a DNA fragment which codes for luciferase. The DNA fragment is inserted into a pre-existing cloning vehicle under the control of an expression promoter, thereby producing a recombinant or derivatized cloning vehicle. A host microorganism is transformed with the derivatized cloning vehicle, cultured and purified for the expression of bioluminescence.

16 Claims, 3 Drawing Figures

PROCESS FOR PRODUCING A CLONED LUCIFERASE-SYNTHESIZING MICROORGANISM

BACKGROUND OF THE INVENTION

This invention relates to a process for cloning luminescence genes. More specifically, this invention relates to a process for cloning luciferase structural genes of a bioluminescent microorganism, such as *Vibrio harveyi*, to produce a transformed microorganism capable of expressing bioluminescence.

It is generally recognized that information which determines the structure of proteins within a cell is contained within the DNA of that organism. Similarly, the information required for control of the synthesis of protein is resident within the DNA. As the genetic code is universal, the nucleotide base sequence within the DNA of one organism will code for production of the same amino acid sequence in another. Therefore, the transfer of DNA from one organism to another is the primary process involved in recombinant DNA technology. The procedure by which this process is accomplished in a laboratory, which is referred to as cloning, involves the formal insertion of fragments of DNA from one organism into a cloning vehicle and transfer of the cloning vehicle into a host cell. In this context, the cloning vehicle may be a plasmid DNA, which is a small circular piece of DNA, or any other DNA sequence which is able to replicate in a host cell.

The fragments of DNA used in cloning are generally derived from cleavage of the DNA molecule, which can be accomplished either by random shearing or by digestion with restriction endonuclease enzymes. Insertion of the DNA fragment in the cloning vehicle is generally accomplished by a process referred to as ligation. Where the cloning vehicle is a plasmid, the DNA ring is opened by digestion with a restriction endonuclease. The newly generated ends of the plasmid DNA are then joined with the ends of the DNA fragments to be cloned by the use of an enzyme such as T4 DNA ligase. I. R. Lehman, *Science* 186, 790 (1974).

One of the primary purposes of cloning DNA fragments is to obtain the expression of a given gene, such as the production of a protein encoded by that gene, in a different organism. Control of the production of that protein, however, requires the existence of a DNA structure referred to as a promoter sequence. The promoter sequence must be positioned properly relative to the inserted fragment of DNA to allow the binding of RNA polymerase from the host organism to the DNA such that messenger RNA molecules and corresponding protein molecules can be produced. The expression of a cloned gene in a host cell then requires, in addition to the cloned gene itself, a promoter sequence that will allow expression of that gene in the host organism. A problem of considerable importance in genetic engineering technology is the difficulty of obtaining a promoter sequence that promotes the expression of the desired genetic information.

Bacterial luciferase is an enzyme which catalyzes the light emitting reaction of naturally bioluminescent bacteria, such as *Vibrio harveyi*. Specifically, luciferase catalyzes the flavin-mediated oxidation by oxygen of a long-chain aldehyde to yield carboxylic acid and blue-green light. ($\lambda$max or 490 nm:1). The reaction in vitro is initiated by injection of reduced flavin mononucleotide, $FMNH_2$ into a vial containing the luciferase, oxygen, and a long-chain aldehyde, usually n-decyl aldehyde. The reaction pathway is as follows:

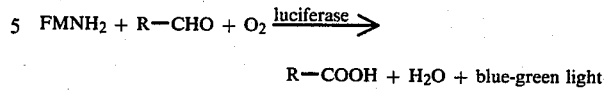

$$R-COOH + H_2O + \text{blue-green light}$$

The reaction in vivo is thought to involve a series of accessory enzymes which supply the luciferase with reduced flavin and the aldehyde substrate.

Since bacterial luciferase is an enzyme, it would appear readily capable of being produced in another organism by recombinant DNA technology. Additionally, the commercial usefulness of being able to produce bacterial luciferase in a controlled fashion employing recombinant DNA technology would be substantial. However, previous efforts to clone the luciferase genes of Beneckea (now referred to as *Vibrio harveyi*) in *E. coli* have been unsuccessful. Lamfrom H. et al., *J. Bacteriology*, 133, 354 (1978). These efforts were performed by producing randomly sheared fragments of Beneckea DNA and inserting them into plasmid DNA. The hybrid plasmids were then used to transform *E. coli*. However, the cloning efforts did not result in luciferase gene expression nor the expression of bioluminescence in *E. coli*.

The present invention represents a significant and distinct contribution to the art in that it provides a means for cloning luciferase genes from microorganisms such as *Vibrio harveyi* to produce constitutive expression of the gene in a host microorganism. As evidence of the expression of the cloned luciferase genes of the present invention, luciferase synthesized within a transformed host microorganism is of the same molecular weight as *Vibrio harveyi* luciferase. In addition, the bioluminescence spectra produced by a transformed host microorganism of the present invention and that of *Vibrio harveyi* are indistinguishable.

BRIEF DESCRIPTION OF THE DRAWINGS

FIG. 1 also shows a Hind III restriction site within the tetracycline resistance region of pBR322.

FIG. 2 also shows alpha and beta subunits of luciferase, lux A and lux B, respectively, within the Hind III restriction fragment.

FIG. 3 also shows insertion of the DNA fragment within the Hind III restriction site of pBR322 in an orientation opposite to transcription of the tetracycline gene.

SUMMARY OF THE INVENTION

Figure 1:
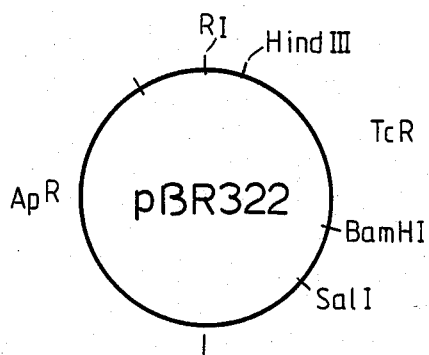
FIG. 1 shows plasmid pBR322, having a molecular length of approximately 4.0 kilobase pairs, and having ampicillin and tetracycline resistance gene regions, $Ap^R$ and $Tc^R$, respectively.

In its broadest scope, the present invention provides a process for producing a cloned luciferase-synthesizing microorganism, capable of the expression of bioluminescence. To perform the process of this invention, genomic DNA of a naturally bioluminescent microorganism, such as *Vibrio harveyi*, is first isolated. The isolated genomic DNA is then digested by restriction to obtain a family of DNA fragments, one of which comprises the complete nucleotide sequence which encodes for luciferase synthesis. The desired fragment is then inserted into a pre-existing cloning vehicle, such as a plasmid DNA, having at least one expression promoter. The pre-existing cloning vehicle may be a recombinant DNA structure having other desired genetic characteristics.

The DNA fragment from the bioluminescent microorganism is inserted into the cloning vehicle such that it is placed under the control of an expression promoter, producing a recombinant or derivatized cloning vehicle. Transfer of the derivatized cloning vehicle to a host microorganism, such as $E.$ $coli$, transforms the host microorganism by a process known as transformation. The transformed microorganism is then cultured and purified for the expression of bioluminescence. By this process, a luciferase-synthesizing microorganism, capable of the expression of bioluminescence, is produced. Where the host microorganism does not produce an appropriate aldehyde, bioluminescence results upon the addition of an aldehyde substrate to the culture medium.

The present invention also provides a cloning vehicle. The preferred cloning vehicle is derived from a plasmid, such as pBR322, however any other DNA sequence capable of replicating in a host microorganism may be utilized. The cloning vehicle of the present invention is comprised of an expression promoter and a DNA fragment of a bio-luminescent microorganism, such as $Vibrio$ $harveyi$, having the complete nucleotide sequence which encodes for luciferase synthesis. The expression promoter is in operable proximity to the DNA fragment, thereby promoting luciferase gene expression. Accordingly, this recombinant or derivatized cloning vehicle constitutes a newly constructed genetic element, capable of expression in a host microorganism.

This invention is also directed to a microorganism transformed by a cloning vehicle of the present invention and produced by the process as described above. The preferred host microorganism is $E.$ $coli$.

The significantly increased amounts of luciferase produced by a transformed microorganism of this invention is of broad commercial use. Specifically, it is useful in clinical assays such as protease assays. Additionally, the capacity of a transformed microorganism to express luminescence makes it possible to utilize the microorganism for a variety of testing, screening, and monitoring techniques. For example, the transformed microorganism offers significant utility as a screening mechanism to determine the pharmaceutical activity of antibiotics. Alternatively, the transformed microorganism is useful to monitor toxic substances in the environment.

Examples of the more important features of this invention have thus been summarized rather broadly in order that the detailed description thereof that follows may be better understood, and in order that the contribution to the art may be better appreciated. There are, of course, additional features of the invention that will be described hereinafter and which will also form the subject of the claims appended hereto.

DETAILED DESCRIPTION OF THE INVENTION

In accordance with the present invention, genomic DNA of an appropriate bioluminescent microorganism, such as the marine bacterium $Vibrio$ $harveyi$, is isolated and purified. The preferred means of accomplishing this is by CsCl ultra-centrifugation as described by Davis, R. W. et al, $Advanced$ $Bacterial$ $Genetics$: Cold Spring Harbor Laboratories 116, 117 (1980).

Figure 2:
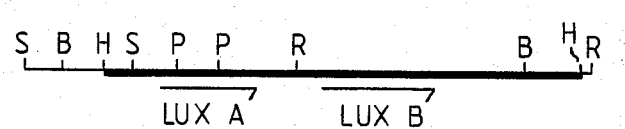
FIG. 2 shows a DNA fragment of *Vibrio harveyi*, having a molecular length of approximately 4.0 kilobase pairs, with Sal I, Bam HI, Hind III, Pst I, and Eco RI restriction sites.

Subsequent to the isolation and purification of the genomic DNA, it is digested by an appropriate restriction endonuclease. Restriction endonucleases are hydrolytic enzymes capable of catalyzing site specific cleavage of a DNA molecule. Therefore, the use of a specific restriction endonuclease is based upon knowledge of its nucleotide sequence specificity and knowledge of the nucleotide sequence corresponding to a specific gene. In the present invention, the restriction endonuclease Hind III is utilized to obtain a family of fragments of $Vibrio$ $harveyi$, one of which comprises the complete nucleotide sequence which encodes for the production of luciferase. The Hind III restriction fragment of $Vibrio$ $harveyi$, having a molecular length of approximately 4.0 kilobase pairs, has been isolated and identified by this inventor as containing the luciferase structural genes. (See FIG. 2).

Once the desired DNA fragment is obtained, it is inserted into a cloning vehicle having at least one expression promoter in accordance with standard cloning techniques. A preferred method is that described by Davis, R. W. et al, $Advanced$ $Bacterial$ $Genetics$: Cold Spring Harbor Laboratories 138, 139 (1980). In the present invention, the preferred cloning vehicle is derived from plasmid pBR322. pBR322 has been fully characterized as a multi-copy replicating plasmid which exhibits both ampicillin and tetracycline resistance attributable to corresponding gene regions and which contains a recognition site for the restriction enzyme Hind III. See J. G. Sutcliff, $Coldspring$ $Harbor$ $Symposium$, 43, 70 (1978). (See FIG. 1) It is recognized that other plasmids equivalent to pBR322 and any other DNA sequence which is capable of replicating in a host microorganism can also be suitably utilized in this invention.

In accordance with the present invention, the Hind III DNA fragment of $Vibrio$ $harveyi$ is inserted into a specific cleavage site of the cloning vehicle such that it is under the control of an expression promoter. Therefore, the recombinant or derivatized cloning vehicle, designated as pTB7, comprises an expression promoter and a DNA fragment of $Vibrio$ $harveyi$ having luciferase structural genes. The expression promoter is in operable proximity to the DNA fragment, thereby promoting luciferase gene expression.

Figure 3:
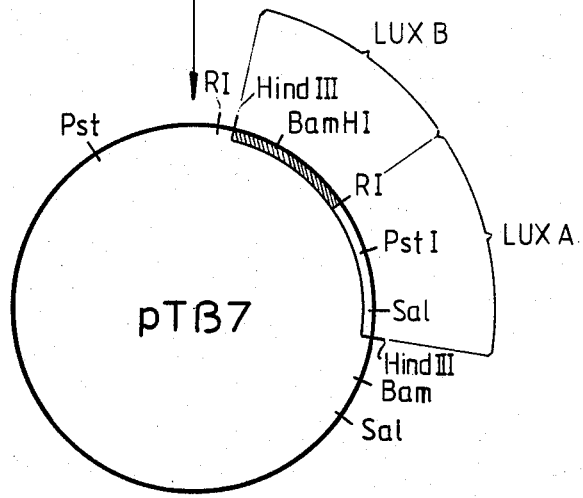
FIG. 3 shows recombinant plasmid pTB7, constructed by insertion of the Hind III DNA fragment of FIG. 2 into pBR322 of FIG. 1.

The specific location of the cleavage site in the cloning vehicle into which the DNA fragment is inserted is the Hind III site. The DNA fragment is inserted into pBR322 within the tetracycline resistance gene region such that it is under the control of an expression promoter within the tetracycline resistance gene region and oriented in a direction opposite to transcription of the tetracycline gene. D. Stuber et al, $Proc.$ $Natl.$ $Acad.$ $Sci.$ $U.S.A.$ 78, 167-171 (1981). (See FIG. 3)

In accordance with this invention, transformation of a microorganism is accomplished by transfer of the recombinant or derivatized cloning vehicle described above to a host microorganism. Accordingly, transformation of a host microorganism, such as $E.$ $coli$ RR1, is accomplished by the transfer of pTB7 to $E.$ $coli$ RR1. The transformed microorganism, designated as $E.$ $coli$ RR1/pTB7, was deposited on Nov. 29, 1982 with the National Regional Research Lab, Peoria, Ill. (NRRL B-15231). While the strain *E. coli* RR1 was utilized in the present invention, it is recognized that other strains of *E. coli*, such as HB101, MM294, ED8654 and JM83 can also be suitably utilized as host microorganisms.

Subsequent to the transformation of a host microorganism, it is cultured in an ampicillin-containing medium. Microorganisms transformed by pTB7 are then purified for the expression of bioluminescence. This is accomplished by the addition of n-decyl aldehyde to the culture medium to stimulate the expression of bioluminescence where the transformed microorganism does not produce an appropriate aldehyde.

Bacterial Strains Employed in Preferred Process

*Vibrio harveyi*, strain 392, was obtained from J. W. Hastings, Harvard University, and grown on sodium chloride complete medium by methods as described by Nealson, K. H. *Meth. Enzymol.* 57, 153–165 (1978). The strain was observed to luminesce naturally as described by Nealson, K. H. *Meth. Enzymol.* 57, 153–165 (1978).

The microorganism into which the expression of luminescence was induced was a well-known strain of *Escherichia coli*, strain RR1, obtained from Jeffrey Herdstran, Texas A&M. The *E. coli* was maintained both as frozen stocks and on L-broth agar plates.

DNA Purification

Genomic DNA containing the complete DNA luciferase gene region is essential to the successful operation of the process of this invention. It is critical, therefore, that selective techniques be employed in obtaining the luciferase DNA. In the preferred method of the present invention, genomic DNA was isolated from *Vibrio harveyi* by lysozyme-SDS lysis of the cells, phenol extraction, ethanol precipitation essentially as described by Davis, R. W. et al, *Advanced Bacterial Genetics*: Cold Spring Harbor Laboratories 116, 117 (1980). The purification process appears also to be important, and it is recommended that CsCl centrifugation of the isolated genomic DNA be carried out as further outlined by Davis, R. W. et al, *Advanced Bacterial Genetics*: Cold Spring Harbor Laboratories 116, 117 (1980).

Plasmid DNA, pBR322, was selected as the cloning vehicle. A suitable fresh supply of pBR322 was isolated from the potential host microorganism *E. coli* RR1 cells by the alkaline extraction method as described by Birmboim and Doly. Birnboim, H. C. et al *Nucl. Acids Res.* 7, 1513–1523 (1979).

EXAMPLE 1: Construction of Recombinant Plasmids

10 µg of purified DNA of *Vibrio harveyi*, isolated as set forth above, was digested with the restriction endonuclease Hind III for two hours at 37° C. Hind III described herein, is commercially available from New England Biolabs, Beverly, Mass. The resulting digest was then heated to 65° C. to inactivate the restriction enzyme and thereafter diluted with 400 µl ligase buffer. This mixture was then combined with 1 µg of the plasmid DNA, pBR322, after that plasmid had been digested with Hind III and treated with calf intestine alkaline phosphatase. Ligation was effected with T4 DNA ligase at 22° C. for two hours.

EXAMPLE 2: Transformation of *E. coli* Cells

200 µl of the ligation mixture prepared in Example 1, above, were used to transform 0.5 ml of freshly thawed, competent, *E. coli* RR1 cells. The two mixtures were combined and then incubated at 45° C. for three minutes after which the combined mixture was diluted into 10 ml L-broth. This diluted mixture was agitated for one hour, at 37° C., after which time 50 µl of the culture were spread onto each of 120 plates of ampicillin-containing Luria agar. The cells were allowed to grow for approximately 16 hours at 37° C.

There were approximately 50–75 colonies per plate. The plates were taken to a photographic darkroom and observed visually for bioluminescence. After no bioluminescence was observed, a small quantity of n-decyl aldehyde was smeared under the lid of each plate. This procedure stimulated bioluminescence in 12 colonies, all of which contained the same recombinant plasmid which has been designated as pTB7.

Analysis of Luciferase Synthesized By Transformed *E. coli*

Antiluciferase IgG was prepared in rabbits and purified and characterized as described by Reeve, C. A. et al., *J. Biol. Chem.* 257, 1037–1043 (1982). The IgG was shown to be effective in precipitation of proteolytic fragments of the luciferase subunits as well as the intact polypeptides. Reeve, C. A. et al., *J. Biol. Chem.* 257, 1037–1043 (1982). The luciferase cross-reacting material contained within *E. coli* carrying pTB7 was analyzed by the immune replication method. Towbin, H., et al., *Proc. Natl. Acad. Sci. U.S.A.* (1979). A 5 ml culture was grown in L-broth to late log phase. Cells contained in 1.5 ml were pelleted in an Eppendorf centrifuge tube and resuspended in 0.5 ml at 50 mM Tris-HCl, pH 8.0 containing 1 mg/ml lysozyme. After 15 minutes on ice, the cells were subjected to approximately 10 seconds of sonication. Assay of the supernatent for luciferase activity indicated that the luciferase concentration in the lysate was about 0.1 mg/ml. The proteins contained 10 µl of the lysate were resolved by polyacrylamide gel electrophoresis, Laemmli, U. K. *Nature* 227, 680–685 (1970), and transferred electrophoretically to nitrocellulose. Bittner, M., et al., *Analytical Biochemistry* 102, 459–471 (1980); Towbin, H., et al., *Proc. Natl. Acad. Sci. U.S.A.* (1979). The nitrocellulose was equilibrated with the antiluciferase IgG and then with 125 I-labelled protein A (Sigma). The 125 I was incorporated using the iodogen method to about 10 cpm/µg. After washing, the nitrocellulose was placed against Kodak XAR-5 film.

Bioluminescence Emission Spectra—The bioluminescence emission spectra of wild-type *Vibrio harveyi* and the aldehyde deficient mutant M17 (Cline, T. W. et al., *J. Bacteriol.* 118, 1059–1066 (1976)) were compared with *E. coli* RR1 carrying pTB7 using SLM Instrument's Model 8000 photon counting spectrofluorometer. The luminescence in vivo was recorded with the excitation light off from cells grown on agar containing appropriate medium. Sections of agar were cut from plates, inserted into cuvettes, and luminescence stimulated in M-17 and pTB7 with n-decyl vapor. Emission in vitro was analyzed using a coupled assay (Hastings, J. W., Baldwin, T. O. et al., *Meth. Enzymol.* 57, 135–152 (1978) which took advantage of the endogenous NADH:FMN oxidoreductase activity in *E. coli*. A sample of a centrifuged lysate from *E. coli* carrying pTB7 was mixed with NADH, FMN and n-decanal and the emission spectrum of the resulting luminescence was recorded. For comparison, a sample of affinity purified wild-type *Vibrio harveyi* luciferase was mixed with a centrifuged lysate from *E. coli* without pTB7, containing the same amounts of NADH, FMN, and n-decyl aldehyde.

The foregoing description has been directed to particular embodiments of the invention in accordance with the requirements of the Patent Statutes for the purposes of illustration and explanation. It will be apparent, however, to those skilled in this art that many modifications and changes will be possible without departing from the scope and spirit of the invention. It is intended that the following claims be interpreted to embrace all such modifications and changes.

What is claimed is:

1. A process for producing a cloned luciferase-synthesizing microorganism capable of expressing bioluminescence comprising:

isolating genomic DNA of *Vibrio harveyi*;
   digesting said genomic DNA to obtain a DNA fragment comprising an approximate 4.0 kilobase pair restriction fragment encoding for both the alpha and beta subunits of luciferase-synthesizing gene;
   inserting said DNA fragment into a DNA cloning vehicle able to replicate in a host microorganism proximate to a promoter thereby producing a derivatized cloning vehicle;
   transforming a host microorganism with said derivatized cloning vehicle to produce a transformed microorganism which expresses bioluminescence;
   culturing said transformed microorganism; and
   purifying said transformed microorganism for the expression of bioluminescence.

2. The process of claim 1 wherein said DNA cloning vehicle is plasmid DNA.

3. The process in claim 1 wherein said DNA cloning vehicle is pBR322.

4. The process in claim 1 wherein said derivatized cloning vehicle is pTB7.

5. The process in claim 1 wherein said DNA fragment is approximately a 4.0 kilobase pair Hind III fragment.

6. The process in claim 1 wherein said DNA fragment is approximately a 4.0 kilobase pair fragment selected from one of SalI-EcoRI; SalI-Hind III; SalI-BamHI; BamHI-EcoRI; BamHI-Hind III; BamHI-BamHI; Hind III-EcoRI; or Hind III-BamHI.

7. A cloning vehicle having a DNA sequence which is able to replicate in a host microorganism, said cloning vehicle comprising:

a DNA fragment from *Vibrio harveyi* comprising approximately 4.0 kilobase pair restriction fragment encoding for both the alpha and beta subunits of luciferase-synthesizing gene; and
   an expression promoter in operable proximity to said DNA fragment.

8. The cloning vehicle of claim 7 wherein said DNA sequence is plasmid DNA.

9. The cloning vehicle of claim 7 wherein said DNA fragment is approximately a 4.0 kilobase pair Hind III fragment.

10. The cloning vehicle of claim 7 wherein said DNA fragment is approximately a 4.0 kilobase pair selected from SalI-EcoRI; SalI-Hind III; SalI-BamHI; BamHI-EcoRI; BamHI-Hind III; BamHI-BamHI; Hind III-EcoRI; or Hind III-BamHI.

11. The cloning vehicle of claim 8, wherein said cloning vehicle is derived from pBR322.

12. The cloning vehicle of claim 11 wherein the promoter is located in the tetracycline resistance region of pBR322.

13. The cloning vehicle of claim 8, wherein said cloning vehicle is pTB7.

14. A microorganism transformed by a cloning vehicle of claims 7, 8, 9, 10, 11, 12, or 13.

15. A microorganism transformed by a cloning vehicle of claims 7, 8, 9, 10, 11, 12, or 13 wherein expression of said DNA fragment produces bioluminescence upon addition of an aldehyde.

16. A transformed microorganism *E. coli* RR1/pTB7.

* * * * *

UNITED STATES PATENT AND TRADEMARK OFFICE
CERTIFICATE OF CORRECTION

PATENT NO. : 4,581,335
DATED : April 8, 1986
INVENTOR(S) : Thomas O. Baldwin

It is certified that error appears in the above-identified patent and that said Letters Patent is hereby corrected as shown below:

Please insert a new first paragraph at column 1 of the patent:

> The Government may have rights in this invention pursuant to funding support awarded by the National Science Foundation Grant No. PCM 79-25335.

Signed and Sealed this

Eleventh Day of December, 1990

Attest:

HARRY F. MANBECK, JR.

*Attesting Officer*  *Commissioner of Patents and Trademarks*